(12) United States Patent
Carpenter et al.

(10) Patent No.: US 10,295,494 B2
(45) Date of Patent: May 21, 2019

(54) DESCRIPTOR-BASED METHODS OF ELECTROCHEMICALLY MEASURING AN ANALYTE AS WELL AS DEVICES, APPARATUSES AND SYSTEMS INCORPORATING THE SAME

(71) Applicant: Roche Diabetes Care, Inc., Indianapolis, IN (US)

(72) Inventors: Scott E. Carpenter, Pendleton, IN (US); Zheng Zheng Pan, Plano, TX (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 533 days.

(21) Appl. No.: 14/852,044

(22) Filed: Sep. 11, 2015

(65) Prior Publication Data
US 2015/0377820 A1    Dec. 31, 2015

Related U.S. Application Data

(63) Continuation of application No. PCT/EP2014/054956, filed on Mar. 13, 2014.
(Continued)

(51) Int. Cl.
*G01N 27/327* (2006.01)
*G01N 27/416* (2006.01)

(52) U.S. Cl.
CPC ..... *G01N 27/3274* (2013.01); *G01N 27/4163* (2013.01)

(58) Field of Classification Search
None
See application file for complete search history.

(56) References Cited

U.S. PATENT DOCUMENTS

2003/0060692 A1  3/2003 L. Ruchti et al.
2004/0157339 A1  8/2004 Burke et al.
(Continued)

FOREIGN PATENT DOCUMENTS

EP   1156324 A1   11/2001
EP   2042865 A2    4/2009
(Continued)

OTHER PUBLICATIONS

Gunasingham; et al., "Pulsed amperometric detection of glucose using a mediated enzyme electrode", Journal of Electroanalytical Chemistry and Interfacial Electrochemistry, Jul. 25, 1990, vol. 287, No. 2, pp. 349-362.

*Primary Examiner* — Eli S Mekhlin

(57) ABSTRACT

Methods are disclosed for measuring an analyte concentration in a fluidic sample. Such methods allow one to correct and/or compensate for confounding variables such as hematocrit, salt concentration and/or temperature before providing an analyte concentration. The measurement methods use response information from a test sequence having at least one DC block, where DC block includes at least one excitation pulse and at least one recovery pulse, and where a closed circuit condition of an electrode system is maintained during the at least one recovery pulse. Information encoded in the excitation and recovery pulses are used to build within- and across-pulse descriptors to correct/compensate for hematocrit, salt concentration and/or temperature effects on the analyte concentration. Methods of transforming current response data also are disclosed. Further disclosed are devices, apparatuses and systems incorporating the various measurement methods.

18 Claims, 10 Drawing Sheets

Related U.S. Application Data

(60) Provisional application No. 61/801,321, filed on Mar. 15, 2013.

(56) References Cited

U.S. PATENT DOCUMENTS

| | | |
|---|---|---|
| 2005/0279631 A1 | 12/2005 | Celentano |
| 2007/0102292 A1 | 5/2007 | Dreibholz et al. |
| 2009/0030641 A1 | 1/2009 | Fjield et al. |
| 2011/0162978 A1 | 7/2011 | Cardosi et al. |

FOREIGN PATENT DOCUMENTS

| | | |
|---|---|---|
| EP | 2138841 A2 | 12/2009 |
| EP | 2261646 B1 | 7/2015 |
| JP | 2001-021525 A | 1/2001 |
| JP | 2007524825 A | 8/2007 |
| JP | 2011-506966 A | 3/2011 |
| WO | 1999032881 A1 | 7/1999 |
| WO | 2001021827 A1 | 3/2001 |
| WO | 2003060154 A2 | 7/2003 |
| WO | 2006109279 A2 | 10/2006 |
| WO | 2007100651 A1 | 9/2007 |
| WO | 2008036516 A1 | 3/2008 |
| WO | 2009075951 A1 | 6/2009 |
| WO | 2010/137266 A1 | 12/2010 |
| WO | 2012/084194 A1 | 6/2012 |
| WO | 2012134890 A1 | 10/2012 |

DESCRIPTOR-BASED METHODS OF ELECTROCHEMICALLY MEASURING AN ANALYTE AS WELL AS DEVICES, APPARATUSES AND SYSTEMS INCORPORATING THE SAME

CROSS-REFERENCE TO RELATED APPLICATIONS

This patent application is a continuation of Int'l Patent Application No. PCT/EP2014/054956 (filed 13 Mar. 2014), which claims priority to and the benefit of U.S. Provisional Patent Application No. 61/801,321 (filed 15 Mar. 2013). Each patent application is incorporated herein by reference as if set forth in its entirety.

TECHNICAL FIELD

This disclosure relates generally to mathematics and medicine, and more particularly, it relates to methods of electrochemically measuring an analyte in a fluidic sample based upon an algorithm incorporating across- and within-pulse descriptors derived from AC and/or DC response information of an electrical test sequence.

BACKGROUND

Significant benefits can be realized from electrochemically measuring analytes in fluidic samples (i.e., biological or environmental). For example, individuals with diabetes can benefit from measuring glucose. Those potentially at-risk for heart disease can benefit from measuring cholesterols and triglycerides among other analytes. These are but a few examples of the benefits of measuring analytes in biological samples. Advancements in the medical sciences are identifying a growing number of analytes that can be electrochemically analyzed by, for example, determining analyte concentrations in a fluidic sample.

The accuracy of current methods of electrochemically measuring analytes such as glucose can be negatively affected by a number of confounding variables including variations in reagent thickness, wetting of the reagent, rate of sample diffusion, hematocrit (Hct), temperature, salt and other confounding variables. These confounding variables can cause an increase or decrease in an observed magnitude of, for example, a current that is proportional to glucose, thereby causing a deviation from the "true" glucose concentration.

Current methods and systems provide some advantages with respect to convenience; however, there remains a need for new methods of electrochemically measuring an analyte in a fluid sample even in the presence of confounding variables.

BRIEF SUMMARY

In view of the disadvantages noted above, the disclosure describes methods of electrochemically measuring an analyte in a fluidic sample such as a body fluid. The methods are based upon an inventive concept that includes building within- and across-pulse descriptors derived from information obtained from an electrical test sequence having at least one DC block, where the at least one DC block includes a sequence of at least one excitation potential and at least one recovery potential under a closed circuit. For example, information such as current response, shape and/or magnitude of the excitation pulses and/or recovery pulses can be used to determine the effects of Hct, salt concentration and/or temperature on the analyte concentration. This information can be built into descriptors for use in algorithms for determining an analyte concentration such as a glucose concentration. The inventive concept therefore provides certain advantages, effects, features and objects when compared to known methods of measuring an analyte concentration (or value) in a fluidic sample.

In one aspect, an electrochemical analysis method is provided for measuring, determining, calculating or otherwise predicting an analyte concentration in a fluidic sample that has been applied to an electrochemical biosensor. The method can include at least a step of providing a test sequence of at least one DC block to the fluidic sample, where the test block is designed to elicit specific information about Hct, salt concentration and/or temperature effects, where the DC block includes at least one excitation potential and at least one recovery potential, and where a closed circuit condition of an electrode system of the biosensor is maintained during the DC block. The method also can include a step of measuring response information to the test sequence or obtaining response information therefrom.

In some instances, the at least one DC block is pulsed as a continuous, unipolar excitation waveform (i.e., the potential is applied and controlled throughout the DC block in a closed circuit), which is in contrast to some pulsed amperometric methods that employ an open circuit between excitation pulses. The DC block includes a plurality of short-duration excitation pulses and recovery pulses optimized for detecting an analyte such as glucose, the optimization pertaining to pulse duration, ramped transitions between the excitation pulse and recovery pulse, number of current responses measured during each pulse, and where in each pulse current response measurements are taken. The DC block can be from at least one (1) pulse to about ten (10) pulses at a potential that alternates between about 0 mV to about +450 mV in a closed circuit. Each of the DC pulses can be applied for about 50 msec to about 500 msec. Moreover, the ramp rate can be from about 10 mV/msec to about 50 mV/msec.

In some instances, the test sequence also can include at least one AC block. In other instances, the test sequence also can include a second DC block. In still other instances, the test sequence includes both the at least one AC block and the second DC block.

In addition, the method can include a step of building at least one within-pulse descriptor and/or at least one across-pulse descriptor that is based upon response currents to the excitation and/or recovery potentials of the DC block to correct and/or compensate for Hct, salt concentration and/or temperature effects on the analyte concentration. The descriptors encode magnitude and shape information of current responses to the test sequence.

Advantageously, by using and applying the descriptors, analyte concentration varies only by ±10% or less for sample Hct varying from about 20% to about 70%, sample salt varying from about 140 mg/dL to about 180 mg/dL, and/or sample temperatures varying from about 6° C. to about 44° C.

In view of the foregoing, devices, apparatuses and systems used in connection with electrochemical analysis are provided that incorporate one or more of the descriptor-based measurement methods disclosed herein. These devices, apparatuses and systems can be used to determine concentration of analytes including, but not limited to, amino acids, antibodies, bacteria, carbohydrates, drugs, lipids, markers, nucleic acids, peptides, proteins, toxins, viruses and other analytes, as well as combinations thereof. In certain instances, the analyte is glucose.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
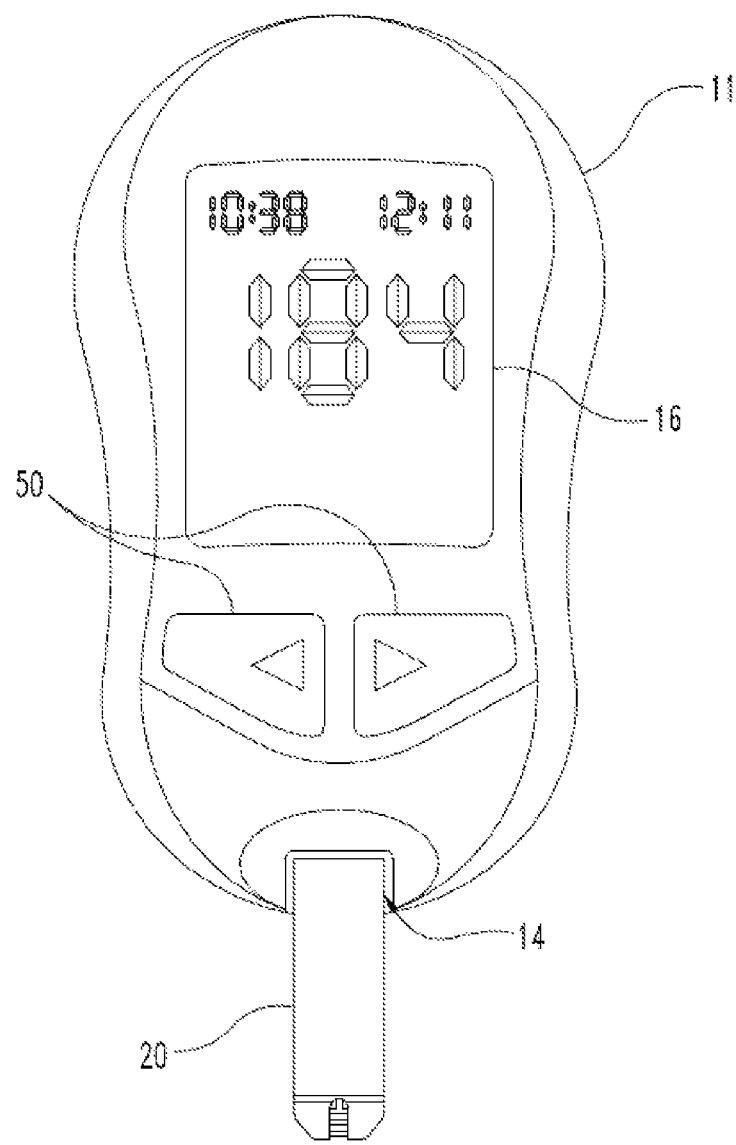
FIG. 1 shows an exemplary analyte test system comprising a meter and a biosensor.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments above and the claims below. Reference should therefore be made to the embodiments above and claims below for interpreting the scope of the inventive concept. As such, it should be noted that the embodiments described herein may have advantages, effects, features and objects useful in solving other problems.

DESCRIPTION OF PREFERRED EMBODIMENTS

The methods, devices, apparatuses and systems now will be described more fully hereinafter with reference to the accompanying drawings, in which some, but not all embodiments of the inventive concept are shown. Indeed, the methods, devices, apparatuses and systems may be embodied in many different forms and should not be construed as limited to the embodiments set forth herein; rather, these embodiments are provided so that this disclosure will satisfy applicable legal requirements.

Likewise, many modifications and other embodiments of the methods, devices, apparatuses and systems described herein will come to mind to one of skill in the art to which the disclosure pertains having the benefit of the teachings presented in the foregoing descriptions and the associated drawings. Therefore, it is to be understood that the methods, devices, apparatuses and systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, devices, apparatuses and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Analyte measurement methods are disclosed herein that use information derived from DC current responses to provide an analyte concentration in a reliable manner. These measurement methods also can be used to reduce the effects of confounding variables such as Hct, salt concentration, temperature and/or variations in reagent thickness, thereby providing a more "true" analyte concentration.

The measurement methods disclosed herein largely utilize amperometry; however, it is contemplated that the methods can be used with other electrochemical measurement methods (e.g., coulometry, potentiomerty or voltammetry). Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6,254,736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953.

Advantageously, the methods described herein can be incorporated into SMBG devices, apparatuses and systems to more accurately and quickly report an analyte concentration, such as a glucose concentration, especially a blood glucose concentration.

Moreover, the measurement methods can be implemented using advanced microprocessor-based algorithms and processes that result in dramatically improved system performance. These measurement methods also offer flexibility and number of ways to create algorithms that can achieve improved performance such as 10/10 performance. As used herein, "10/10 performance" means that a measured bG value is within about ±10% of the actual bG value for bG concentrations >100 mg/dL, and within ±10 mg/dL of the actual bG value for bG concentrations <100 mg/dL.

Details regarding additional electrochemical measurement methods that may be useful in performing the methods disclosed herein can be found in the following co-filed and co-pending patent applications titled: "METHODS OF SCALING DATA USED TO CONSTRUCT BIOSENSOR ALGORITHMS AS WELL AS DEVICES, APPARATUSES AND SYSTEMS INCORPORATING THE SAME" (Int'l Patent Application No. PCT/EP2014/054952); "METHODS OF ELECTROCHEMICALLY MEASURING AN ANALYTE WITH A TEST SEQUENCE HAVING A PULSED DC BLOCK AS WELL AS DEVICES, APPARATUSES AND SYSTEMS INCORPORATING THE SAME" (Int'l Patent Application No. PCT/EP2014/054965); "METHODS OF FAILSAFING ELECTROCHEMICAL MEASUREMENTS OF AN ANALYTE AS WELL AS DEVICES, APPARATUSES AND SYSTEMS INCORPORATING THE SAME" (Int'l Patent Application No. PCT/EP2014/054955); "METHODS OF USING INFORMATION FROM RECOVERY PULSES IN ELECTROCHEMICAL ANALYTE MEASUREMENTS AS WELL AS DEVICES, APPARATUSES AND SYSTEMS INCORPORATING THE SAME" (Int'l Patent Application No. PCT/EP2014/054943); and "METHODS OF DETECTING HIGH ANTIOXIDANT LEVELS DURING ELECTROCHEMICAL MEASUREMENTS AND FAILSAFING AN ANALYTE CONCENTRATION THEREFROM AS WELL AS DEVICES, APPARATUSES AND SYSTEMS INCORPORTING THE SAME" (Int'l Patent Application No. PCT/EP2014/054962).

Analyte Measurement Devices, Apparatuses and Systems

Prior to, and in connection with, describing the inventive measurement methods, FIG. 1 shows an exemplary analyte measurement system including a device such as a test meter 11 operatively coupled with an electrochemical biosensor 20 (also known as a test element). Meter 11 and biosensor 20 are operable to determine concentration of one or more analytes in a fluidic sample provided to the biosensor 20. In some instances, the sample may be a body fluid sample such as, for example, whole blood, plasma, serum, urine or saliva. In other instances, the fluidic sample may be another type of sample to be tested for the presence or concentration of one or more electrochemically reactive analyte(s) such as an aqueous environmental sample.

In FIG. 1, the biosensor 20 is a single use test strip removably inserted into a connection terminal 14 of meter 11. In some instances, biosensor 20 is configured as a blood glucose test element and includes features and functionalities for electrochemically measuring glucose. In other instances, biosensor 20 is configured to electrochemically measure one or more other analytes such as, for example, amino acids, antibodies, bacteria, carbohydrates, drugs, lipids, markers, nucleic acids, peptides, proteins, toxins, viruses, and other analytes.

Meter 11 includes an electronic display 16 that is used to display various types of information to the user including analyte concentration(s) or other test results, and user interface 50 for receiving user input. Meter 11 further includes a microcontroller and associated test signal generating and measuring circuitry (not shown) that are operable to generate a test signal, to apply the signal to the biosensor 20, and to measure one or more responses of the biosensor 20 to the test signal. In some instances, meter 11 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, meter 11 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary meters configured for use with electrochemical measurement methods are disclosed in, for example, U.S. Pat. Nos. 4,720,372; 4,963,814; 4,999,582; 4,999,632; 5,243,516; 5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

One of skill in the art understands that the measurement methods described herein can be used in other measurement, devices, apparatuses, systems and environments such as, for example, hospital test systems, laboratory test systems and others.

It shall be understood that the meter and biosensor can include additional and/or alternate attributes and features in addition to or instead of those shown in FIG. 1. For example, the biosensor can be in the form of a single use, disposable electrochemical test strip having a substantially rectangular shape. It shall be appreciated that the biosensors can include different forms such as, for example, test strips of different configurations, dimensions or shapes, non-strip test elements, disposable test elements, reusable test elements, micro-arrays, lab-on-chip devices, bio-chips, bio-discs, bio-cds or other test elements. Additional details regarding exemplary biosensors configured for use with electrochemical measurement methods are disclosed in, for example, U.S. Pat. Nos. 5,694,932; 5,762,770; 5,948,695; 5,975,153; 5,997,817; 6,001,239; 6,025,203; 6,162,639; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,063,774; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026, as well as RE42560, RE42924 and RE42953.

Figure 2:
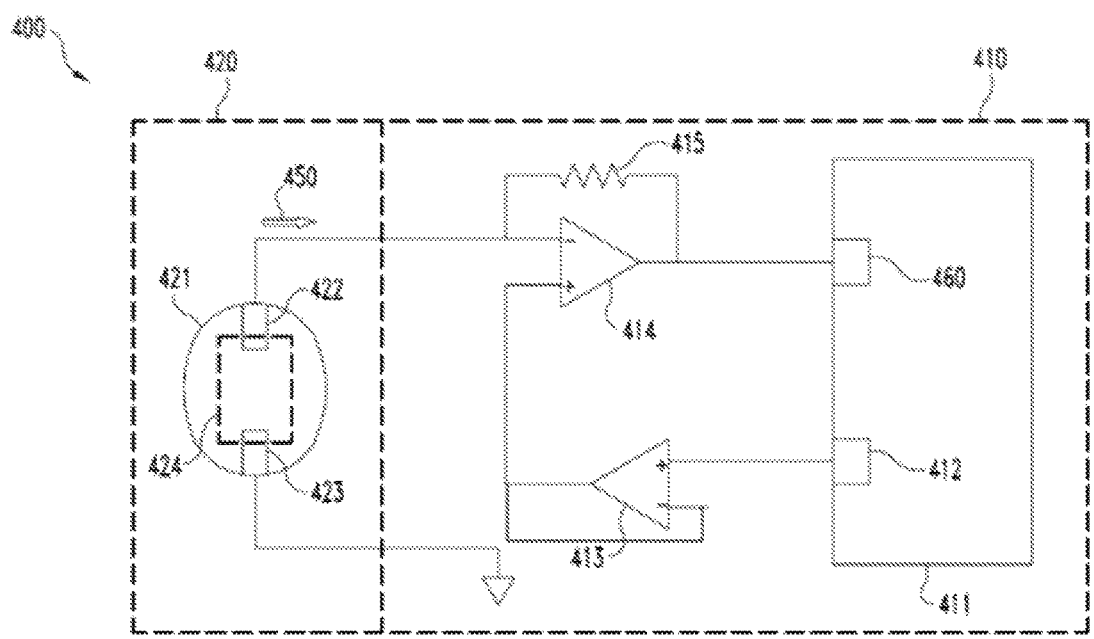
FIG. 2 shows a simplified circuit diagram for an exemplary analyte measurement system.

FIG. 2 shows a simplified circuit diagram 400 of an exemplary analyte measurement system including a biosensor 420 operatively coupled with a meter 410 to provide electrical communication between biosensor 420 and meter 410. Biosensor 420 includes a test cell 421 having a working electrode 422 and a counter electrode 423 in contact with a combined reagent and sample 422. Working electrode 422 is in electrical communication with the negative input of amplifier 414 of meter 410. Counter electrode 423 is in electrical communication with a virtual ground or reference potential of meter 410.

Meter 410 includes a microcontroller 411, which is operable to generate and output a test control signal at output 412. The test control signal drives amplifier 413 to output a test potential to the positive input of amplifier 414. This test potential also is seen at the negative input of amplifier 414 due to a virtual short between the positive input and negative input of amplifier 414. The test potential present at the negative input of amplifier 414 provided to working electrode 422. Thus, the test control signal output by microcontroller 411 is operable to control the test potential applied to the working electrode 422. The test control signal provided at output 412 and test potential provided to working electrode 422 may include a number features such as AC components, preconditioning components, and DC pulse sequences including excitation potentials and closed circuit recovery potentials, examples of which are further described herein below.

The test potential applied to working electrode 422 produces a current response 450 that is provided to the negative input of amplifier 414. Amplifier 414 is configured as an I/V converter and outputs a voltage to input 460 of microcontroller 411 that is proportional to current response 450. Microcontroller 411 detects the voltage at input 460 and determines the current response 450 by dividing the voltage seen at input 460 by the value of gain resistor 415. The current response 450 may include responses to test potentials including AC components, preconditioning components, and DC pulse sequences including excitation potentials and closed circuit recovery potentials, examples of which are further described herein below.

It shall be appreciated that additional exemplary analyte measurement systems may include a number of features in addition to or as alternatives to those illustrated in simplified circuit diagram 400. For example, microcontroller 411 also may be operatively connected to other components of meter 410 such as one or more digital memories, displays and/or user interfaces, such as those illustrated and described above in connection with FIG. 1, as well as controller and driver circuitry associated therewith. In FIG. 2, output 412 is an analog output connected to a D/A converter internal to microcontroller 412, and input 460 is an analog input connected to an A/D converter internal to microcontroller 412. In other instances, output 412 may be a digital output connected to an external D/A converter and input 460 may be a digital input connected to an external A/D converter. In FIG. 2, test cell 421 is a two-electrode test cell; however, other test cells can be three-electrode test cells, or other electrode systems.

In FIG. 2, a test potential can be applied to a working electrode to provide a potential difference between the working electrode and a counter electrode. Alternatively, a test potential other than virtual ground or reference potential can be provided as a counter electrode to provide a potential difference between the working electrode and a counter electrode. It shall be appreciated that the foregoing and a variety of other additional and alternate test cell, electrode, and/or circuitry configurations operable to apply a test signal to an electrode system in contact with a combined sample and reagent and measure a response thereto may be utilized.

Measurement Methods

As noted above, the measurement methods described herein are based upon an inventive concept that includes using information derived from DC responses to a test sequence having at least one DC block, where the block is designed to provide specific information about aspects of a sample and/or biosensor.

Figure 3:
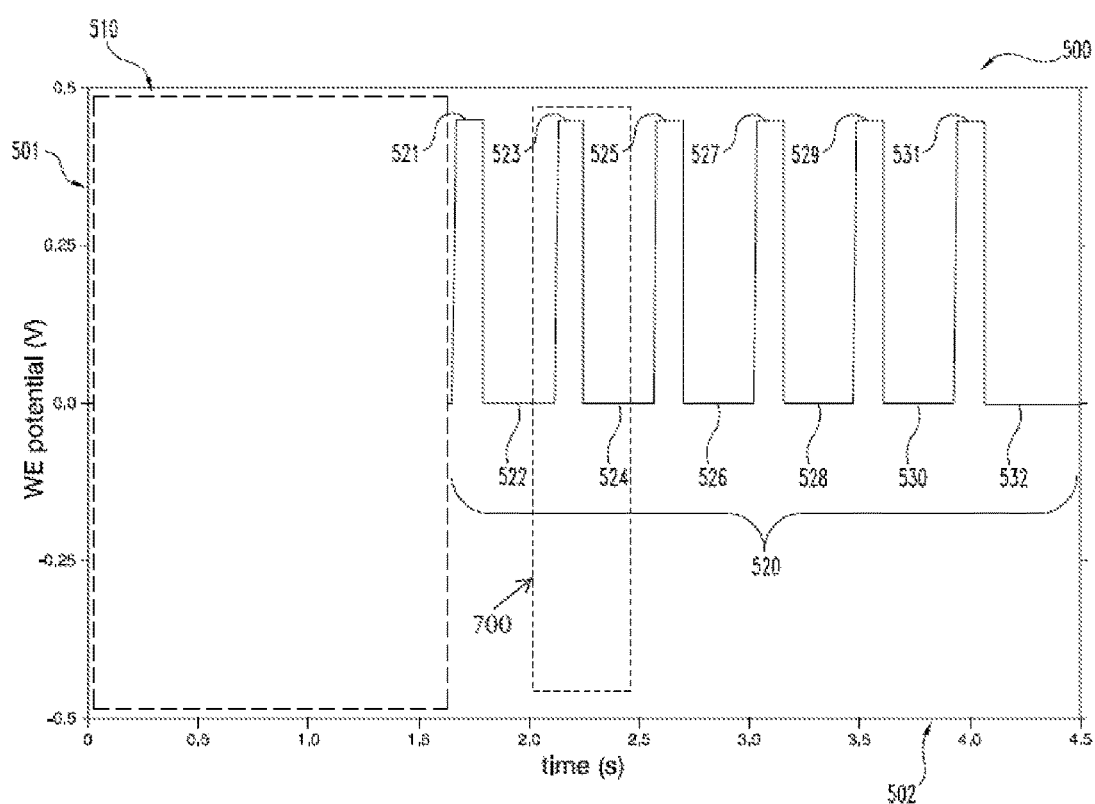
FIG. 3 is a graph of an exemplary test sequence of an analyte measurement system.
Figure 4:
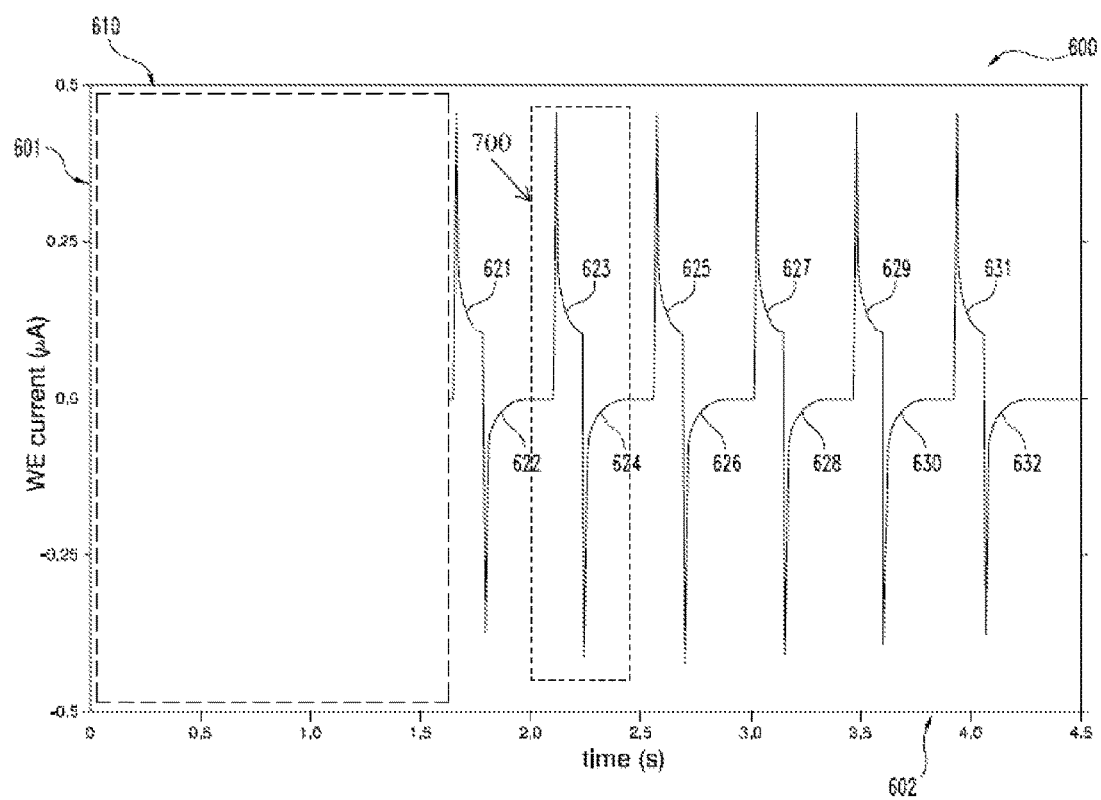
FIG. 4 is a graph of an exemplary response of an analyte measurement system to the test sequence of FIG. 3.

The methods generally include applying to a fluidic sample, such as a body fluid, an AC block in connection with a pulsed DC sequence and measuring the AC and DC current responses. As shown in FIGS. 3-4, one trace illustrates the applied DC potential, and the other trace illustrates the AC and DC current responses, respectively. The applied DC potential can be fixed at about 0 mV between pulses to provide a recovery pulse, thus making it a generally continuous, unipolar excitation waveform. This is in contrast to a test sequence from known methods that prescribe the use of an open circuit between positive DC pulses, thereby excluding the possibility of collecting and analyzing the current between positive pulses.

As used herein, "recovery pulse" means an about zero-potential pulse applied for an adequately long recovery period in which the electrochemical reaction with the analyte of interested (e.g., glucose) is turned "off," thereby allowing the system to return to a fixed starting point before subsequent interrogation with another more positive DC pulse.

The test sequence thus generally includes a block of low-amplitude AC signals followed by a controlled, DC block.

With respect to the AC block, it can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC block can include about 2 segments, about 3 segments, about 4 segments, about 5 segments, about 6 segments, about 7 segments, about 8 segments, about 9 segments, or about 10 segments. In still other instances, the AC block can have more than 10 segments, that is, about 15 segments, about 20 segments, or about 25 segments. In yet other instances, the AC block can include 1 segment, where the segment has multiple low-amplitude AC signals applied simultaneously.

One of skill in the art understands that the number of AC segments will be limited by the complexity of the response, the associated frequency range and time available to perform the measurements. Higher frequencies generally require high bandwidth electronics and faster sampling, whereas lower frequencies take longer and typically are noisier. The maximum number of segments therefore will be a compromise of these parameters, choosing the minimum count and frequency span needed to discriminate the sample and environmental and/or confounding factors of interest.

As used herein, "about" means within a statistically meaningful range of a value or values such as a stated concentration, length, molecular weight, pH, potential, time frame, temperature, voltage or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The frequency of each signal in each segment of the AC block can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC block can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC block can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC block, however, can be up to about 100 kHz for an inexpensive, battery-powered handheld instrument. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC block typically includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies the desired low-amplitude AC signals. The AC frequencies may be applied sequentially, or combined and applied simultaneously and analyzed via Fourier Transform.

The AC block can be applied for about 500 msec to about 1.5 sec, about 600 msec to about 1.25 sec, about 700 msec to about 1000 msec, or about 800 msec to about 900 msec. Alternatively, the AC block can be applied for about 500 msec, about 600 msec, about 700 msec, about 800 msec, about 900 msec, about 1000 msec, about 1.25 sec or about 1.5 sec. In particular, the AC block can be applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a biosensor will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

Additional details regarding exemplary AC blocks in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

With respect to the DC block, it can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC block can include about 2 pulses, about 3 pulses, about 4 pulses, about 5 pulses, about 6 pulses, about 7 pulses, about 8 pulses, about 9 pulses, or about 10 pulses. In still other instances, the DC block can have more than 10 pulses, that is, about 15 pulses, about 20 pulses, or about 25 pulses. As used herein, "pulse" means at least one excitation and one recovery period.

The DC block typically includes a constantly applied potential difference that alternates between about 0 mV and about +450 mV potential difference, or other slowly time-varying potential difference that can be analyzed by traditional DC electrochemical methods. One of skill in the art, however, understands that the range for the applied potential difference can, and will, vary depending upon the analyte and reagent chemistry used. As such, excitation pulse potential can be greater-than, less-than or equal to about +450 mV. Examples of excitation potentials include, but are not limited to, 50 mV, 75 mV, 100 mV, 125 mV, 150 mV, 175 mV, 200 mV, 225 mV, 250 mV, 275 mV, 300 mV, 325 mV, 350 mV, 375 mV, 400 mV, 425 mV, 450 mV, 475 mV, 500 mV, 525 mV, 550 mV, 575 mV, 600 mV, 625 mV, 650 mV, 675 mV, 700 mV, 725 mV, 750 mV, 775 mV, 800 mV, 825 mV, 850 mV, 875 mV, 900 mV, 925 mV, 950 mV, 975 mV or 1000 mV.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at +450 mV can be applied for about 250 msec, and each DC pulse at 0 mV can be applied for about 500 msec. Alternatively still, each pulse can be applied for less than about 50 msec or more than about 500 msec.

Generally, the ramp rate of each DC pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

Like the AC block, one of skill in the art understands that the number, potential, duration and order of the DC pulses can be varied.

AC and/or DC current response information is collected from the test sequence and includes current responses to the AC and DC blocks. In some instances, the current response information can be collected at an A/D sampling rate for DC and AC measurements to simplify the system design, including a single shared signal path for AC and DC measurements. Common digital audio sampling rates range include, but are not limited to, from about 44.1 kHz to about 192 kHz. A/D converters in this range are readily available from variety of commercial semiconductor suppliers.

As part of the inventive concept, it has been recognized that the recovery responses include unique informational content, particularly pertaining to Hct, salt concentration and temperature. Furthermore, this information provides value and can be used to further refine accuracy and performance of SMBG devices, apparatuses and systems.

Returning to FIG. 3, the responses to the pulsed DC block encode Hct and temperature information, as well as real-time information about other important processes, such as wetting of the reagent, sample diffusion and separation with respect to the reagent, the establishment of a stable glucose transport gradient, and the kinetics associated with the reducible analyte. The illustrated DC block provides short, distinct strobing of these processes with respect to time. Each positive DC pulse produces a distinct current signature, which is not exactly like the others due to its position in time.

Importantly, each closed circuit recovery potential pulse provides an adequately long recovery period in which the electrochemical reaction with glucose is turned off, thereby allowing the system to return to a common starting point before subsequent interrogation with another positive pulse.

Just as the shapes of the current decays from positive DC pulses encode information about glucose, Hct and temperature (as well as the other biosensor processes noted above), the shapes of the recovery pulses also are unique. Each recovery pulse produces a negative current response with a rate of growth that also encodes distinct, time-ordered information describing how the biamperometric system returns to a given reference state. The rate of current growth during the recovery pulse is not simply a mirror image of the current decay associated with a neighboring positive DC pulse, because the glucose reaction has been turned off by selecting a potential magnitude that cannot initiate and sustain the electrochemical reaction with glucose. The exemplary methods disclosed herein utilize unique information pertaining to Hct, temperature and other confounding variables encoded by differences within and across the excitation and/or recovery current responses to improve the accuracy and performance SMBG devices, apparatuses and systems.

It shall be appreciated that near-zero, and non-zero positive and negative potential magnitudes also may be utilized as recovery pulses in additional embodiments, and that the magnitude, duration, and shapes of all pulses may vary from the illustrated exemplary embodiments. It also shall be appreciated that the exemplary embodiments disclosed herein do not restrict the number of AC frequencies that may be employed, their positions in time, or their amplitude(s)/frequencies. Nor does it restrict interspersing AC frequencies within the DC block of the test sequence, such as in the exemplary test s illustrated in FIG. 3 and discussed in greater detail below. Furthermore, the exemplary embodiments disclosed herein do not restrict the number, length or magnitude of the DC pulses.

FIG. 3 shows an exemplary test sequence 500 that can be provided to an electrode system of an electrochemical test cell. The vertical axis 501 of graph denotes working electrode potential in volts (V). It shall be understood that working electrode potential may refer to a potential applied to a working electrode or to a potential difference between a working electrode and another electrode such as a counter or reference electrode regardless of the electrode or electrodes to which a potential or a test signal is applied. The horizontal axis 502 of graph denotes time in sec. Test sequence 500 is applied at or after time=0 sec, which is a time at which a sufficient sample is present in a test cell as may be determined using sample sufficiency detection electrodes and signals or through other techniques.

Test sequence 500 begins with a signal component 510 (or block) that may include one or more AC segment(s), preconditioning test segment(s) or combinations thereof. Signal component 510 also may include incubation signal components that are selected not to drive an electrochemical reaction but to allow for reagent hydration and progression of reaction kinetics. Such incubation components may include, for example, an open circuit condition, a 0 mV potential, a substantially 0 mV average potential, or a non-zero volt potential such as a non-zero potential that is less than the potential needed to drive a particular reaction of interest.

In some instances, signal component 510 comprises one or more AC segments and frequencies provided to an electrode system of an electrochemical test cell. For example, the AC segments of signal component 510 include a 10 kHz segment applied from about time=0 sec to about time=1.2 sec, a 20 kHz segment applied from about time=1.2 sec to about time=1.3 sec, a 10 kHz segment applied from about time=1.3 sec to about time=1.4 sec, a 2 kHz segment applied from about time=1.4 sec to about time=1.5 sec, and a 1 kHz segment applied from about time=1.5 sec to about time=1.6 sec. Alternatively, the AC segments and frequencies of signal component 510 includes a 10 kHz signal applied for about 1.5 sec, followed by a 20 kHz signal applied for about 0.2 sec, followed by a 10 kHz signal applied for about 0.2 sec, followed by a 2 kHz signal applied for about 0.2 sec, followed by a 1 kHz signal applied for about 0.2 sec.

As noted above, the signal component 510 can include one or more preconditioning signal(s). In some instances, the signal component 510 includes a positive DC preconditioning pulse applied starting at about time=0 sec for about 200-600 msec and having an amplitude of about 100 mV or greater. In other instances, the signal component 510 includes a positive DC preconditioning pulse applied starting at about time=0 sec for about 500 msec and having an amplitude of about 450 mV. In still other instances, the signal component 510 includes a two cycle triangular potential wave including a slew rate of about 2 V/s.

As such, the signal component 510 can include combinations of one or more AC segments as well as preconditioning signal component(s). In some instances, the signal component 510 includes one or more AC signal components followed by one or more preconditioning signal components. In other instances, the signal component 510 includes one or more preconditioning signal components followed by one or more AC signal components.

After signal component 510, a pulsed DC sequence 520 (or block) is applied to the electrode system. Pulse sequence 520 begins with the working electrode potential being ramped up to the excitation potential of pulse 521. From pulse 521 the working electrode potential is ramped down to the recovery potential of pulse 522. From potential 522 the working electrode potential is sequentially ramped up and down to the potentials of pulses 523-532. As shown in FIG. 3, the ramping between pulses is controlled to occur at a predetermined rate effective to mitigate capacitive current response. In some instances, the ramp rate is selected to provide a 50% or greater reduction in peak current relative to the peak current provided by a substantially square wave excitation in which signal rise time is determined by the native characteristics of the driving circuitry rather than being deliberately controlled according to a predetermined target rate or range.

Pulses 521, 523, 525, 527, 529 and 531 are examples of ramp-rate controlled excitation potential pulses that provide an excitation potential to an electrochemical test cell effective to drive an electrochemical reaction in the test cell and generate an associated Faradaic current response which may be convolved with capacitive charging current responses and other current response information attributable to a plurality of confounding variables. As also shown in FIG. 3, the excitation potential pulses provide a potential difference between a working electrode and a counter electrode of about 450 mV that is about 130 msec in duration. The excitation potential shown is selected to drive a particular analyte reaction, which in this case is an enzyme-mediated reaction of glucose. It shall be understood that the magnitude and duration of the excitation potential pulses may vary depending upon the particular activation potential of the mediator used or the potential needed to drive a particular reaction of interest.

Pulses 522, 524, 526, 528, 530 and 532 are examples of closed circuit recovery potential pulses that provide a potential to a working electrode of an electrochemical test cell during which a closed circuit condition of the test cell is maintained to control the test cell to discharge current and to more rapidly restore test cell conditions to a substantially common starting point for subsequent interrogation with an excitation potential pulse. Closed circuit recovery potential pulses also may be ramp rate controlled in the same or a similar manner to excitation potential pulses. As shown in FIG. 3, the recovery potential pulses provide a potential difference between a working electrode and a counter electrode of about 0 mV, which is about 280 msec in duration during which the electrode system is maintained in a closed circuit condition.

In some instances, the magnitude of the DC potential provided by a closed circuit recovery pulse and its duration may vary depending upon the potential below which a test cell can recover toward a pre-excitation state and the time needed to provide a desired response. Thus, some embodiments can include recovery potential pulses having a non-zero potential that is less than the activation potential of a given mediator. Some instances include recovery potential pulses having a non-zero potential that is less than the potential needed to drive a particular reaction of interest. Other instances include recovery potential pulses having a non-zero potential that is less than the minimum redox potential for a specified reagent system. Still other instances include recovery potential pulses having an average potential of about 0 mV, but which have pulse portions greater than 0 mV and portions less than 0 mV. Still other instances include recovery potential pulses having an average potential according to any of the aforementioned non-zero potentials, but which have portions greater than the non-zero average and portions less than the non-zero average.

FIG. 4 shows a current response 600 produced by a test cell in response to test sequence 500 of FIG. 3. The vertical axis 601 of graph 600 denotes working electrode current in µA. The horizontal axis 602 of graph 600 denotes time in seconds. Current response 600 begins with response component 610 that includes a response to signal component 510. In some instances, response component 610 includes AC current responses from which impedance, admittance and phase angle can be determined. Such measurements may be performed for one or more AC block segments or components such as those described above in connection with FIG. 3. In some instances, response component 610 includes a preconditioning signal component but no AC segment and no measurement of response component 610 is performed. In other instances, response component 610 includes a combination of the foregoing and/or other components.

After response component 610, response 600 includes a sequence of exponentially decaying excitation current responses 621, 623, 625, 627, 629 and 631, which are generated in response to excitation pulses 521, 523, 525, 527, 529 and 531, respectively. Excitation current responses 621, 623, 625, 627, 629 and 631 include a Faradaic current response component relating to an electrochemical reaction in the test cell as well as a capacitive charging current response relating to capacitive electrode charging and current response information attributable to a plurality of confounding variables. Current responses 622, 624, 626, 628, 630 and 632 include a recovery current response relating to discharge of the test cell when maintained in a closed circuit condition applying a recovery potential and current response information attributable to a plurality of confounding variables.

Current responses 621-632 include information related to the concentration of an analyte of interest that may be present in the fluidic sample being tested, as well as additional information of confounding variables convolved therewith. This inventive concept described herein therefore can be incorporated into methods by which the information associated with current responses 621-631 can be used to determine a concentration of an analyte of interest with enhanced accuracy, precision, repeatability and reliability by compensating for or decreasing sensitivity to one or more confounding variables. A number of confounding variables may impact analyte concentration determinations including variations in reagent film thickness, sample temperature, sample Hct, reagent wetting, and reaction kinetics among others. The present disclosure demonstrates that the methods disclosed herein may be utilized to perform analyte concentration determinations that compensate for or exhibit decreased sensitivity to such confounding variables.

Figure 5:
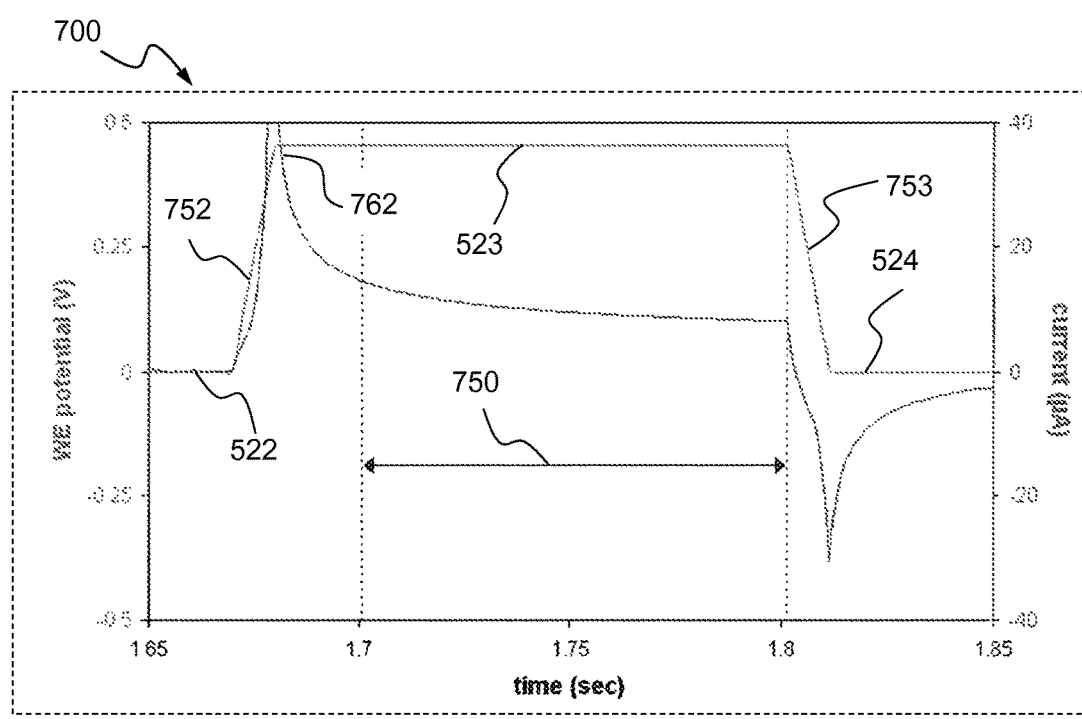
FIG. 5 is an enlarged view illustrating portions of the test sequence of FIG. 3 and the response of FIG. 4.

FIG. 5 shows in greater detail a portion 700 of the signals illustrated in FIGS. 3-4. The closed circuit recovery potential 522 ramps to excitation potential 523 over a rate controlled ramp potential 752 such as, for example, a ramp rate of about 45 V/sec. Alternatively, the ramp potentials can be controlled to have a ramp rate less than about 50 V/sec, between about 40 V/sec to about 50 V/sec, or between about 40 V/sec to about 45 V/sec. Other embodiments control the ramp rate between pulses at different rates that are effective to reduce the contribution of the effect of capacitive charging on current responses.

The ramping rate of ramp potential 752 is effective to reduce the effect of capacitive charging on current response 762, which is generated in response to ramp potential 752 and excitation potential 523. Average current is measured starting about 30 msec after excitation potential 523 is achieved over an about 100 msec measurement period ending at the point at which excitation potential 523 begins to ramp down to closed circuit recovery potential 522 over ramp potential 753. Similar current measurements may be taken for excitation current responses 621, 625, 627, 629 and 631. It shall be appreciated that average current measurements may be performed using continuous integration, discrete integration, sampling or other averaging techniques. The successive current measurements may be used to construct an effective current decay curve from which analyte concentration can be calculated using techniques such as Cottrell analysis and others. In FIG. 5, ramp potential 753 is controlled to have a ramp rate substantially the same as ramp potential 752. In other instances, ramp potential 753 may be controlled at different rates or may be allowed to transition at a system defined rate without active control.

Current responses, such as current responses 621-632, therefore encode unique time ordered information relating to sample glucose concentration, sample Hct, sample temperature, as well as information relating to processes such as reagent wetting of the reagent, sample diffusion and separation with respect to the reagent, the establishment of a stable glucose transport mechanism, and the kinetics associated with the reducible analyte. Pulse sequences such as pulse sequence 520 provide short, distinct strobing of these processes with respect to time and produces current responses including unique, time-ordered information relating to sample glucose concentration, sample Hct, sample temperature, and other factors. The inventors have demonstrated a number of unexpected advantages of the techniques disclosed herein through experiments in which pulse sequences such as pulse sequence 520 were used to analyze various concentrations of blood glucose while Hct and temperature were varied systematically.

Figure 6:
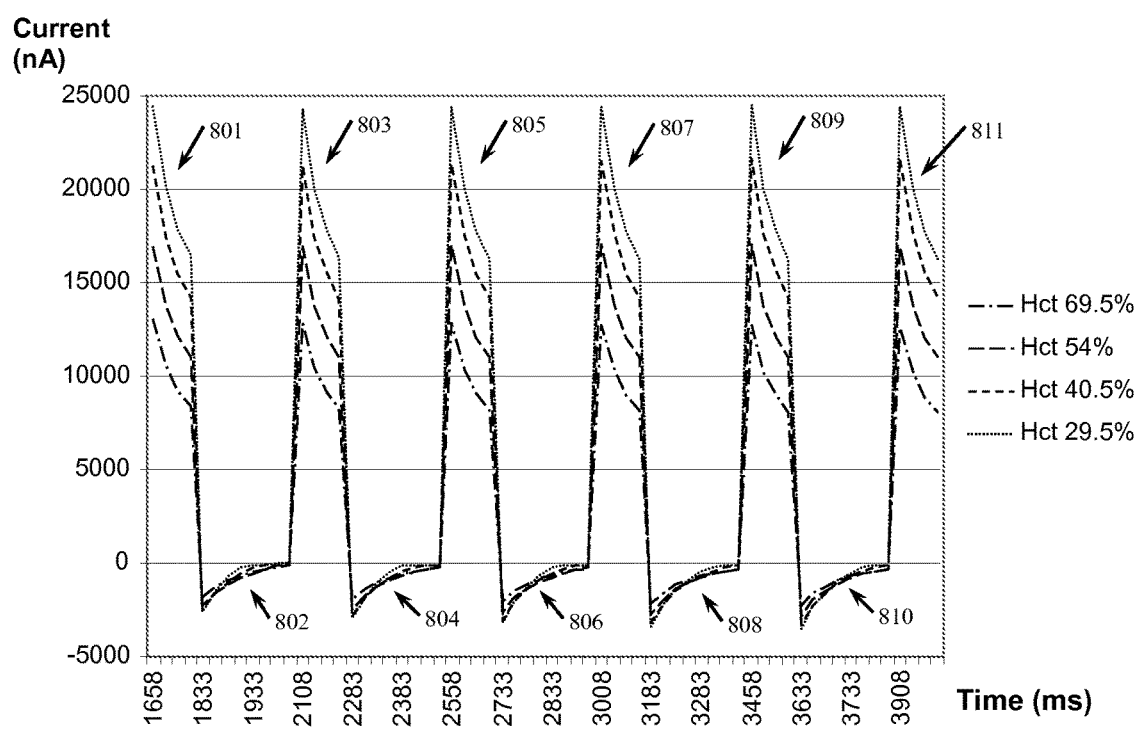
FIG. 6 is a graph illustrating current responses for test samples with varying Hct concentrations, constant temperatures, and constant glucose concentrations.

FIG. 6 shows the effects of an exemplary systematic variation of excitation current responses and recovery current responses to pulse sequence 520 described above for varying Hct and constant temperature. Current responses are illustrated for four test samples with varying Hct concentrations of about 29.5%, 40.5%, 54% and 69.5%, constant glucose concentrations of about 530 mg/dL, and constant temperatures of about 25° C. The magnitude and decay rates of the excitation current responses to excitation potential pulses 521, 523, 525, 527, 529 and 531 vary with sample Hct in a manner that is substantially constant with respect to time. At each Hct, current responses 801, 803, 805, 807, 809 and 811 exhibit substantially consistent magnitudes and decay rates for each pulse in pulse sequence 520. Within each pulse of pulse sequence 520, the magnitude of current responses 801, 803, 805, 807, 809 and 811 varies in an inverse relationship with Hct.

The magnitude and growth rates of the recovery current responses to recovery potential pulses 522, 524, 526, 528, 530 and 532 also exhibit an observable relationship. Recovery current responses 802, 804, 806, 808 and 810 to closed circuit recovery potential pulses 522, 524, 526, 528, 530 and 532 have comparable starting magnitudes both within each pulse and across pulses for each Hct, but have different rates of growth resulting in current response crossovers. As Hct varies, current responses 802, 804, 806, 808 and 810 grow at different rates depending upon the Hct.

The aforementioned current response characteristics and relationships also were demonstrated in experiments that used samples having constant glucose concentrations of about 33 mg/dL but were otherwise substantially in accordance with those described above.

Figure 7:
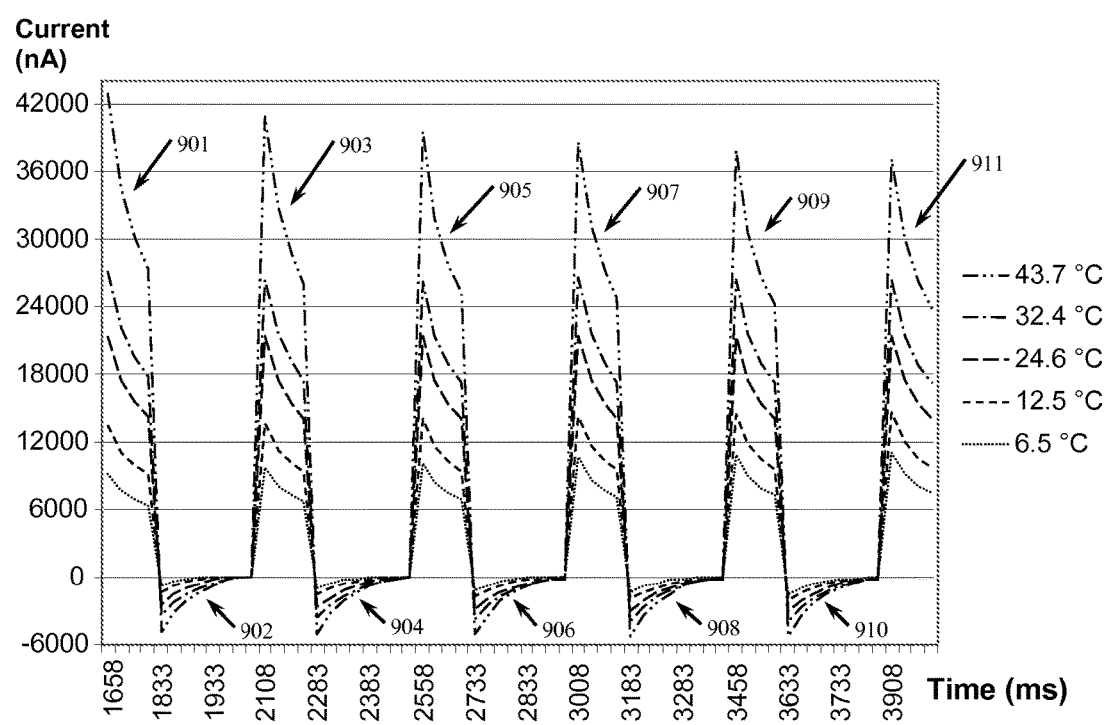
FIG. 7 is a graph illustrating current responses for test samples with varying temperatures, constant Hct concentrations and constant glucose concentrations.

In comparison, FIG. 7 shows the effects an exemplary systematic variation of current responses to pulse sequence 520 for varying temperature, constant Hct and constant glucose concentration. Current responses are illustrated for five test samples with varying temperatures of 6.5° C., 12.5° C., 24.6° C., 32.4° C. and 43.7° C., constant Hct of about 41%, and constant glucose concentrations of about 535 mg/dL. The current responses to the positive DC potential of pulses 521, 523, 525, 527, 529 and 531 show a relative decrease for successive pulses with respect to time. The magnitude of current responses 901, 903, 905, 907, 909 and 911 decrease successively across pulses for each of the sample temperatures. Furthermore, the amount of decrease across pulses varies depending upon sample temperature.

The magnitude and growth rates of the recovery current responses to recovery potential pulses 522, 524, 526, 528, 530 and 532 also exhibit an observable relationship. Recovery current responses to 522, 524, 526, 528, 530 and 532 show substantially consistent magnitudes across pulses and, within each pulse, have distinctly ordered starting values and decreasing growth rates, but exhibit no crossover.

The aforementioned current response characteristics and relationships also were demonstrated in experiments that used samples having constant glucose concentrations of about 33 mg/dL but were otherwise substantially in accordance with those described above.

From this research, a number of analyte concentration measurement methods will now be described that use "descriptors" to encode magnitude and shape information of excitation current responses and closed circuit recovery current responses to the short duration pulse sequences of excitation potentials and closed circuit recovery potentials such as those described above in, for example, FIGS. 3-5. Descriptors represent a way to encode information relating to analyte concentration as well as information relating to systematic variation in confounding variables such as variation in sample Hct, sample temperature, sample salt, chemical kinetics, diffusion and other confounding variables. Such information may be contained within magnitude and shape of current responses to short-duration excitation and recovery pulses, for example, as illustrated and described above in connection with FIGS. 6-7. Analyte concentration determinations using descriptors provide a unique and unexpected compensation for insensitivity to the effects of confounding variables.

The descriptors described herein include (1) within-pulse descriptors, and (2) across-pulse descriptors. As used herein, "within-pulse descriptor" or "within-pulse descriptors" means numerical quantities determined using one or more observed measurements within a current response to an individual pulse (excitation or recovery) in a continuous DC waveform, to describe an intrinsic property of the current response. Two examples of within-pulse descriptors include the average current value within a current response and the magnitude difference between two different current responses separated in time during the same pulse (e.g., the first and last measured current values within a current response). Additional examples of within-pulse descriptors include, but are not limited to, the slopes and intercepts from any two measurement points within a current response, for example, the first two points, the last two points, the first and last points, and other sets of points within a current response; the amplitudes and time constants from a multi-exponential fit of the current response using relative or absolute time values; the sum of all current measurements and the cumulative slope and intercept of those currents within a pulse, an angle between a certain portion of a current response and a horizontal or vertical axis; and extrapolated value from a certain portion of a current response.

As used herein, "across-pulse descriptor" or "across-pulse descriptors" means numerical quantities encoding information of the progression or development of current responses to two or more pulses as a function of time. Across-pulse descriptors may encode information for current responses to sequential pulses or for pulses separated by intervening pulses or time. An example of an across-pulse descriptor includes magnitude and/or slope differences for points or sets of points of current responses to two or more pulses, for example, the magnitude differences between the last current value in an excitation pulse and the first current value in an adjacent recovery pulse, as well as the magnitude differences between the last point in a recovery pulse and the first point in the following excitation pulse. Additional examples of across-pulse descriptors include, but are not limited to, the current responses from all pulses, only positive pulses, only recovery pulses or other combinations, for example, the slope, intercept and/or parameter values from a curve fit through the first or last current values from all positive pulses or negative pulses, respectively.

Descriptors also may be used in connection with methods involving transformations of current response information. An ideal model of the relationship between current as a function of time and analyte concentration is given by the Cottrell equation, which provides that $I=nFAc_o(D/\pi t)^{-1/2}$, where I is current in amps, n is the number of electrons to reduce/oxidize one molecule of a given analyte, F is Faraday's constant (96,485 C/mol), A is the area of a planar electrode in $cm^2$, $c_o$ is the initial concentration of the analyte in $mol/cm^3$, D=diffusion coefficient for the analyte in $cm^2/s$, and t=time in sec. A simplified form of the Cottrell equation is $i=kt^{-1/2}$, where k is the collection of constants n, F, A, $c_o$ and D for a given system. The Cottrell equation is typically used to analyze graphs of current vs. $time^{-1/2}$. For ideal Cottrell behavior, the resulting slope is linear, but this is not the case for many real world analyte measurement systems.

As described above, descriptors encoding magnitude and shape information of current responses such as slope, intercept and curvature information, can be utilized in performing analyte concentration determinations. The inventors have developed data transformation methods that can be utilized in systems where Cottrell behavior is not linear. Certain transformations utilize descriptors of the slope, linearity and/or curvature in a transformed ln-ln space. Additional examples include slopes and intercepts of best fit lines for two or more current measurements, slopes and intercepts for current averages for ranges within pulses, and other types of slope and intercept descriptors.

Figure 8:
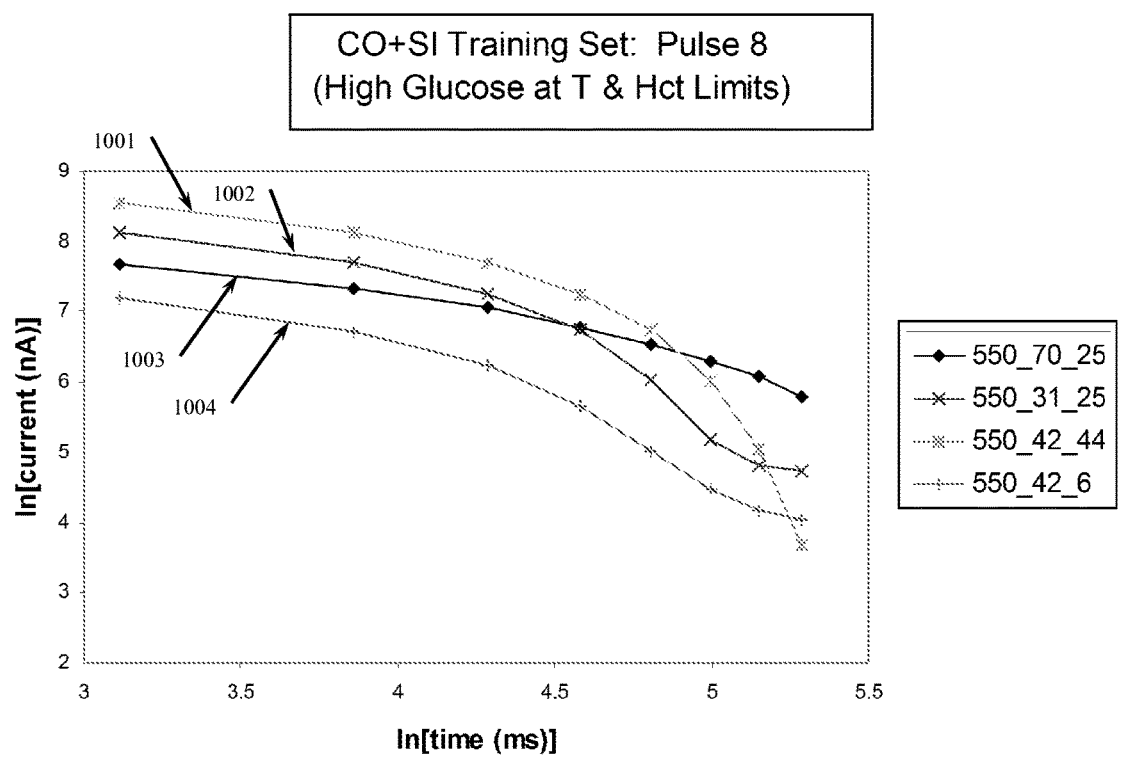
FIG. 8 is a graph illustrating recovery current response information for test samples with varying temperatures and varying Hct concentrations.

FIG. 8 is a graph of current responses to recovery pulse 528 for four samples 1001, 1002, 1003 and 1004 in a transformed coordinate system where x=ln(time) and y=ln(current), time is measured from the start of pulse 528, and current is measured at multiple points during pulse 528. Sample 1101 has a glucose concentration of 550 mg/dL, a Hct concentration of 70%, and a temperature of 25° C. Sample 1102 has a glucose concentration of 550 mg/dL, a Hct concentration of 31%, and a temperature of 25° C. Sample 1103 has a glucose concentration of 550 mg/dL, a Hct concentration of 42%, and a temperature of 44° C. Sample 1104 has a glucose concentration of 550 mg/dL, a Hct concentration of 42%, and a temperature of 6° C.

For recovery pulse 528, samples 1101, 1102, 1103 and 1104 show a nonlinear relationship between ln(current) and ln(time) which includes information relating to sample temperature and sample Hct at a given glucose concentration. For example, there is a systematic change in the separation and order of current responses 1101 and 1102 resulting in a crossover as sample Hct changes and the sample temperature remains constant. In addition, there is a systematic difference in the slope and intercept defined by the last two current measurements for sample 1103 and sample 1104 when the Hct level is constant and temperature is varied. The descriptors disclosed herein may be used to encode information of these systematic relationships and to perform analyte concentration determinations compensating for variation in sample Hct and sample temperature among other confounding variables.

Figure 9:
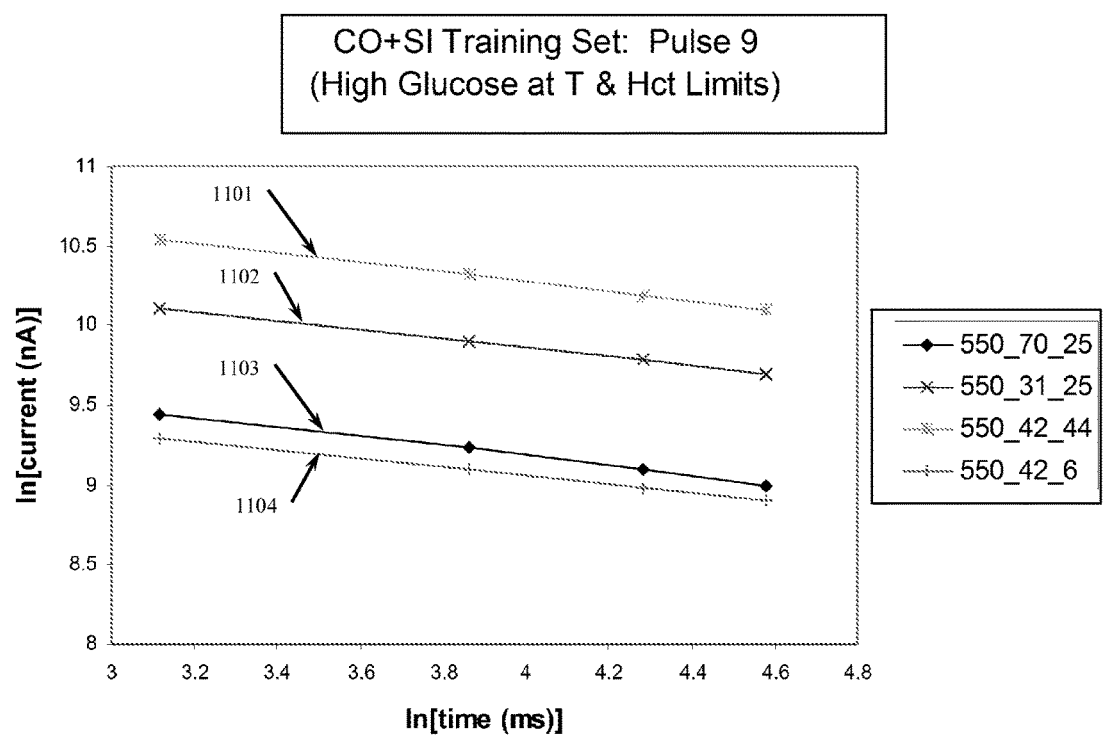
FIG. 9 is a graph illustrating excitation current response information for test samples with varying temperatures and varying Hct concentrations.

FIG. 9 is a graph of current responses to excitation pulse 529 for samples 1101, 1102, 1103 and 1104 plotted in a transformed coordinate system where x=ln(time) and y=ln(current), time is measured from the start of pulse 529, and current is measured at multiple points during pulse 529. Samples 1101, 1102, 1103 and 1104 show a linear relationship between ln(current) and ln(time) for excitation pulse 529 and the relative order of current responses remains constant during pulse 529. The effect of Hct variation can be seen through a comparison of samples 1101 and 1102. The effect of temperature variation can be seen through a comparison of samples 1103 and 1104 and is greater than the effect due to Hct variation. The descriptors disclosed herein may be used to encode information of these systematic relationships and to perform analyte concentration determinations compensating for variation in sample Hct and sample temperature among other confounding variables.

Figure 10:
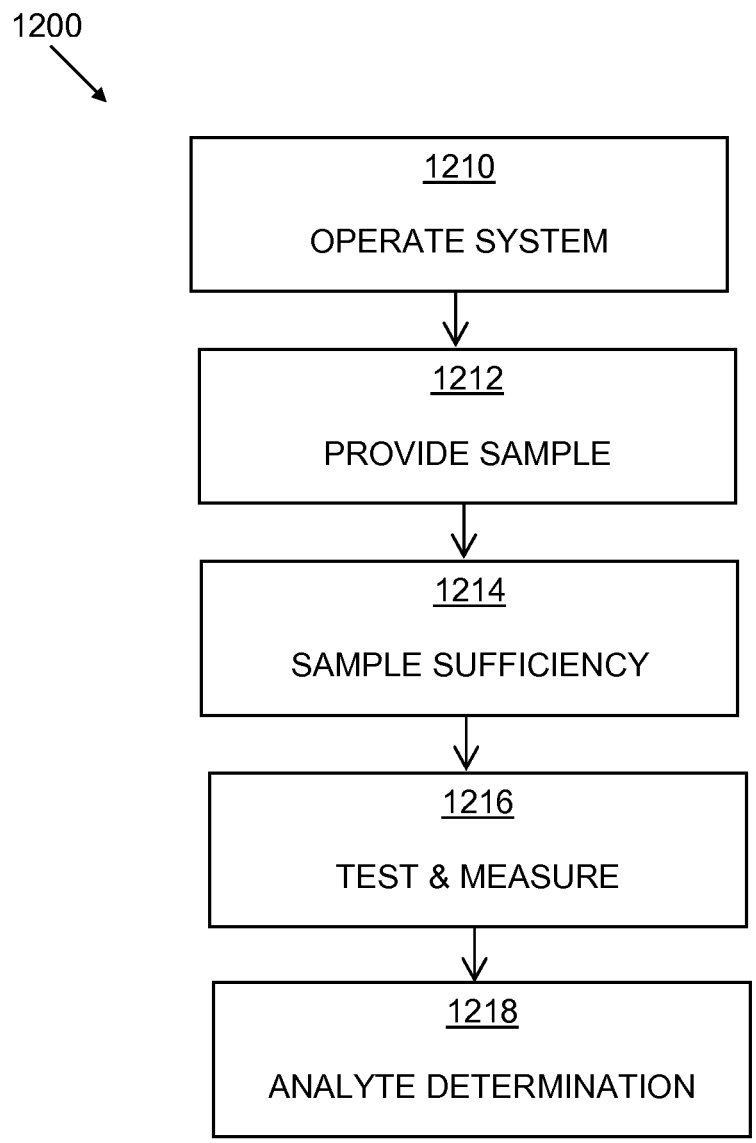
FIG. 10 is a flow diagram illustrating an exemplary method.

The descriptor and/or data transformation methods disclosed herein may be used to determine glucose concentration in a sample of blood provided to a test cell including an electrode system. FIG. 10 illustrates an exemplary glucose concentration determination process 1200, which may be performed using analyte measurement systems including a meter and an electrochemical biosensor such as those described herein.

Process 1200 begins at operation 1210 where a meter is operatively coupled with an electrochemical biosensor. Process 1200 continues to operation 1212 where a sample is provided to the biosensor and contacted with a reagent to provide a test cell including an electrode system in electrical communication with the combined sample and reagent. Process 1200 then continues to operation 1214 where a sample sufficiency determination is performed by the meter. If an affirmative sample sufficiency determination is made process 1200 proceeds to operation 1216 and initiates a test signal and response measurement operation. If an affirmative sample sufficiency determination is not made, operation 1214 repeats and may optionally time out or terminate after a predetermined number of attempts, or after a predetermined time has elapsed, or based upon other criteria.

Operation 1216 performs a test sequence and response measurement operation during which a test sequence is generated by the meter and provided to the electrode system of the test cell, and a response signal of the test cell is measured by the meter. In some instances, operation 1216 generates and provides test sequence 500 to the electrode system and measures the corresponding response 600. The measurement of response 600 may include measurement of response component 610 and measurement of current responses 621-632. Multiple current measurements are taken during each of current responses 621-632, and the measured current information is stored in a memory. It shall be appreciated that in other instances, operation 1216 generates and provides other test signals including a DC pulse sequence having excitation potential pulses and recovery potential pulses and respective corresponding excitation current responses and recovery current responses which may include the variations and alternatives described herein above, as well as other numbers, magnitudes and durations of excitation potential pulses and recovery potential pulses. Process 1200 then proceeds to operation 1218, where a microcontroller and/or other processing circuitry processes the stored current measurement information to determine a glucose concentration.

Operation 1218 determines a glucose concentration based upon the stored current measurement information including current response information corresponding to excitation potential pulses and current response information corresponding to recovery pulses. In some instances, operation 1218 utilizes descriptors that encode the slope and intercept of the last two current measurement points within a current response in an x-y coordinate system where x=ln(time) and y=ln(current) and where time is measured relative to an identified starting point for each pulse (excitation and recovery) to determine an effective DC current according to Equation 1:

$$I_{eff} = \sum_{i=1}^{i=N}(c_{i,m}*P_{i,m}+c_{i,b}*P_{i,b}).$$

In Equation 1, $I_{eff}$ designates the effective DC current, i designates a pulse number in a pulse sequence of the excitation potential pulses and the recovery potential pulses, N designates the total number of pulses in a sequence (including both excitation and recovery pulses), $P_{i,m}$ is a descriptor designating the slope of the last two current measurement points within a pulse in an x-y coordinate system where x=ln(time) and y=ln(current), $P_{i,b}$ is a descriptor designating the intercept of the last two current measurement points within a pulse in an x-y coordinate system where x=ln(time) and y=ln(current), $c_{i,m}$ designates a slope weighting constant, and $c_{i,b}$ designates an intercept weighting constant. The weighting constants may be determined empirically using a number of optimization techniques, for example, those available in the SAS software package available from SAS Institute, Inc.

It shall be appreciated that the number of pulses and associated current responses may vary. In some examples herein, the number of pulses was N=9. Other forms, however, can use a different numbers of pulses. Furthermore, it shall be appreciated that not all pulses in a test sequence need be utilized in an analyte concentration determination, for example, where the number of pulses N=9, and pulse sequence including eleven pulses such as that disclosed above in connection with FIG. 3 may be used, and the current response information for pulses 10 and 11 may not be utilized. In other instances, information from current responses to all pulses in a test signal may be used.

Operation 1218 uses the effective current $I_{eff}$ as well as AC current response information to determine a predicted glucose concentration according to Equation 2:

$$Predglu=a0+(b0+\exp(b1+b2*I_{eff}+P_{eff}+Y_{eff}))*(I_{eff}).$$

In Equation 2, $P_{eff}$ is the effective phase of the AC current response, $Y_{eff}$ is the effective admittance of the AC current response, and a0, b0, b1 and b2 are constants that are determined through known optimization techniques. The phase term, $P_{eff}$, is determined according to Equation 3:

$$P_{eff}=bp2*(p11*\cos(\alpha)+p12*\sin(\alpha))+bp3*(-p11*\sin(\alpha)+p12*\cos(\alpha)).$$

In Equation 3, α=arctan(I), p11 is a 20 kHz AC current response phase, p12 is a 10 kHz AC current response phase, and bp2 and bp3 are optimized weighting coefficients that may be determined by various optimization techniques. The admittance term, $Y_{eff}$, is defined according to Equation 4:

$$Y_{eff}=by2*(y11*\cos(\alpha)+y12*\sin(\alpha))+by3*(-y11*\sin(\alpha)+y12*\cos(\alpha)).$$

In Equation 4, α=arctan(I), and y11 is a 20 kHz AC admittance, y12 is a 10 kHz AC admittance, and by2 and by3 are optimized weighting coefficients that may be determined by various optimization techniques.

Operation 1218 may use alternative methods to determine a predicted glucose concentration, for example, according to relationship described by Equation 5:

$$Predglu=a0+a1*I_{eff}+\exp(b0+P_{eff}+Y_{eff})*I_{eff}.$$

In Equation 5, $P_{eff}$ is the effective phase of the AC current response, $Y_{eff}$ is the effective admittance of the AC current response, and a0, a1 and b0 are constants. $P_{eff}$ and $Y_{eff}$ may be determined using substantially the same techniques as described above.

It shall be appreciated that the descriptors, transformations and determinations described above in connection with operation 1218 are non-limiting examples of methods by which analyte concentrations can be determined using information included in current responses corresponding to a DC pulse sequence comprising excitation potential pulses and current response information for recovery pulses. Alternative methods incorporating the inventive concept may utilize a variety of additional or alternate descriptors and/or data transformations in accordance with the principles and examples disclosed herein.

The inventors developed and experimentally validated that a number of unexpected performance characteristics can be achieved through the methods disclosed herein. A number of such performance characteristics were validated in connection with the general method described in connection with FIG. 10. An exemplary performance characteristic includes 10/10 performance, where less than 5% of glucose determinations performed using a plurality of test elements included an error greater than ±10% at high glucose levels such as those at or above 75 mg/dL and/or an error of ±10 mg/dL at low glucose levels such as those below 75 mg/dL.

Certain exemplary methods therefore include 10/10 performance for variation in sample temperature, variation in sample Hct, and/or variation in sample salt. Some methods include 10/10 performance for 50% variation in sample Hct, for example, variation from 20%-70% Hct. Other methods include 10/10 performance for 50° C. variation in sample temperature, for example, variation from 6° C. to 44° C. Other methods include 10/10 performance for 40 mg/dL variation in sample salt, for example, variation in sample salt from 140 mg/dL to 180 mg/dL. Other methods include 10/10 performance for a combination of the foregoing temperature, Hct and/or salt variations.

Further exemplary performance characteristics include, but are not limited to, measurement bias, normalized error ("NE") standard deviation of normalized error ("SDNE"), total system error ("TSE") and combinations thereof. In one exemplary validation study, 10/10 performance for compensation for co-variation of sample Hct from about 20% to about 70% and sample temperature from about 6° C. to about 44° C. demonstrated the performance characteristics summarized in Table 1 below.

TABLE 1

| 10/10 Temperature Failures | 10/10 Hct Failures | Bias at Nominal | NE | SDNE | TSE |
|---|---|---|---|---|---|
| 0 | 0 | 1.79 | 0.22 | 5.67 | 9.55 |

Another exemplary performance characteristic includes bias, SDNE and TSE characteristics for variation in reagent film thickness. In an exemplary validation study, three rounds of testing were performed with capillary blood for three rolls of test elements produced on up to two different lanes (O and M). Measured dry reagent film thicknesses for rolls 1, 2 and 3 were 4.64, 4.08 and 5.10 μm, which correspond to nominal, −12%, +10%. The performance characteristics for this study are summarized in Table 2 below.

TABLE 2

| Roll | Lane | N | Mean Bias | SDNE | TSE |
|---|---|---|---|---|---|
| 1 | M | 477 | −0.30 | 4.11 | 8.52 |
| 1 | O | 233 | −1.68 | 4.22 | 10.12 |
| 1 | M&O | 710 | −0.75 | 4.20 | 9.14 |
| 2 | O | 236 | 6.17 | 5.49 | 17.15 |
| 3 | M | 234 | −6.32 | 4.39 | 15.10 |

The study demonstrated a negligible bias (−0.75) with capillary blood, even though the analyte concentration technique was not trained with capillary blood. The study also demonstrated low mean biases for both lanes of roll 1 even though the algorithm was trained with strips from lane M only. The study further demonstrate insensitivity to coat weight variation as the mean bias was about +6% at the lower coat weight and about −6% at the higher coat weight.

In another exemplary validation study, three rounds of testing were performed on the test elements from roll 1. This study considered study-to-study variation in testing and demonstrated the results summarized in Table 3 below.

TABLE 3

| Roll | Lane | N | Mean Bias | SDNE | TSE |
|---|---|---|---|---|---|
| 1 | M | 238 | 0.06 | 3.85 | 7.76 |
| 1 | O | 239 | 0.05 | 4.09 | 8.23 |
| 1 | M&O | 477 | 0.06 | 3.97 | 7.99 |

A further exemplary validation study tested ten different lots of test elements, three of which were used in verification of the analyte concentration determination technique. This study demonstrated lot-to-lot robustness results summarized in Table 4 below.

TABLE 4

| Roll | Lane | N | Mean Bias | SDNE | TSE |
|---|---|---|---|---|---|
| 2 | M&O | 480 | −0.73 | 4.44 | 9.61 |
| 3 | M&O | 479 | 2.31 | 3.78 | 9.88 |
| 4 | M&O | 478 | 2.44 | 4.33 | 11.10 |
| 2 | M | 240 | 0.57 | 4.54 | 9.66 |
| 2 | O | 240 | −2.04 | 3.93 | 9.9 |
| 3 | M | 240 | 2.68 | 3.55 | 9.78 |
| 3 | O | 239 | 1.94 | 3.97 | 9.89 |
| 4 | M | 240 | 1.91 | 4.05 | 10.02 |
| 4 | O | 238 | 2.98 | 4.53 | 12.04 |

Another exemplary performance characteristic includes compensation for dose tremble such as double dosing or delayed dosing at various glucose concentrations and Hct levels. An exemplary dose tremble validation study was conducted and demonstrated the results summarized in Table 5 below.

TABLE 5

| Glucose | HCT | Dose Type | Mean Prediction | Standard Deviation | Bias |
|---|---|---|---|---|---|
| 120 | 45 | Normal | 135.22 | 3.65 | 0.00 |
| 120 | 45 | Tremble | 138.24 | 4.18 | 2.23 |
| 120 | 70 | Normal | 124.38 | 3.88 | 0.00 |
| 120 | 70 | Tremble | 127.72 | 3.79 | 2.68 |
| 550 | 45 | Normal | 578.03 | 3.35 | 0.00 |
| 550 | 45 | Tremble | 593.94 | 3.37 | 2.75 |
| 550 | 70 | Normal | 621.51 | 3.70 | 0.00 |
| 550 | 10 | Tremble | 626.13 | 4.23 | 0.74 |

Performance characteristics also were validated in connection with the descriptors and method described in connection with FIG. 10, as well as additional descriptors. The performance characteristics for a variety of exemplary descriptors are summarized in Table 6 below.

TABLE 6

| | Descriptors | | | | |
|---|---|---|---|---|---|
| | LN Time, LN Current Descriptors of FIG. 10 | Simple Linear, R's Compensated AC & DC | 1/sqrt Time with Temperature Descriptors | Rate of Total Charge (Q) Buildup - Orig DC, Rs Modified Y's | All Pulse Transitions - Orig DC Current |
| Failed T Claims | 0 | 0 | 0 | 0 | 0 |
| Failed Hct Claims | 0 | 0 | 0 | 0 | 3 |
| SDNE Training | 4.7 | 3.7 | 3.7 | 8.0 | 6.5 |
| Salt Claim | Passed | Passed | Passed | Passed | Passed |
| Mean Bias CV Round 1 | −0.7 | −0.1 | 0.6 | −0.6 | −5.2 |
| SDNE Round 1 | 4.2 | 4.7 | 4.7 | 4.9 | 4.3 |
| Mean Bias CV Round 2 | 0.1 | 0.1 | 1.6 | −1.1 | −5.8 |
| SDNE Round 2 | 4.0 | 4.4 | 4.1 | 7.1 | 5.9 |
| Mean Bias CV Round 3 | 2.3 | 3.3 | −3.1 | −3.9 | −3.1 |
| SDNE Round 3 | 3.8 | 4.3 | 3.7 | 5.1 | 4.6 |

TABLE 6-continued

| | Descriptors | | | | |
|---|---|---|---|---|---|
| | LN Time, LN Current Descriptors of FIG. 10 | Simple Linear, R's Compensated AC & DC | 1/sqrt Time with Temperature Descriptors | Rate of Total Charge (Q) Buildup - Orig DC, Rs Modified Y's | All Pulse Transitions - Orig DC Current |
| Side Dosing Bias | 0.6 | 3.2 | 2.4 | 0.8 | 1.4 |
| 5 mg/dL Ascorbic Acid Bias at 40 Glu | 8.4 | 24.5 | 17.0 | 1.8 | 0.3 |
| 15 mg/dL Ascorbic Acid Bias at 40 Glu | 34.2 | 59.5 | 53.4 | 18.1 | −1.7 |

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A method of electrochemically measuring an analyte in a fluid sample, the method comprising the steps of:
applying an electrical test sequence to an electrochemical biosensor, the electrochemical biosensor comprising:
an electrode system,
a reagent in electrical communication with the electrode system, and
a receptacle configured to contact the fluid sample provided to the electrochemical biosensor, with the fluid sample in fluidic contact with the reagent, wherein the electrical test sequence comprises at least one direct current (DC) block, the at least one DC block includes at least one excitation potential pulse and at least one recovery potential pulse, each potential configured to produce response information to the electrical test sequence, and wherein a closed circuit condition of the electrode system is maintained during the at least one DC block;
measuring the response information from the at least one DC block of the electrical test sequence;
building descriptors encoding magnitude and shape characteristics of the response information to the electrical test sequence, wherein the descriptors encode transformed slope information and transformed intercept information in the response information for at least one excitation current response or recovery current response;
determining an effective current using the descriptors; and
determining an analyte concentration of the fluid sample based upon the effective current determined using the descriptors, wherein the analyte concentration is a glucose concentration.

2. The method of claim 1, wherein the transformed slope information and the transformed intercept information pertain to an x-y coordinate system, and wherein x=ln(time) and y = ln(current).

3. The method of claim 1, wherein the effective current is proportional to the analyte concentration of the fluid sample.

4. The method of claim 3, wherein the effective current is determined in accordance with the following equation:

$$I_{eff} = \sum_{i=1}^{i=N} (c_{i,m} * P_{i,m} + c_{i,b} * P_{i,b}),$$

wherein $I_{eff}$ designates the effective current, i designates a pulse number in the electrical test sequence of potential pulses, N designates a total number of pulses in the electrical test sequence, $P_{i,m}$ comprises a first descriptor that designates a slope of two current measurement points within pulse i, $P_{i,b}$ comprises a second descriptor that designates an intercept of two current measurement points within pulse i, and $c_{i,m}$ and $c_{i,b}$ designate empirically determined weighting constants.

5. The method of claim 4, wherein N=9 and pulses i=1, 3, 5, 7, and 9 comprise excitation potentials.

6. The method of claim 1, wherein the fluid sample is blood.

7. The method of claim 6, wherein the analyte concentration varies from an actual concentration of the analyte in the blood by +/−10% or less, and wherein the blood comprises hematocrit from about 20% to about 70%.

8. The method of claim 6, wherein the analyte concentration varies from an actual concentration of the analyte in the blood by +/−10% or less, and wherein the blood comprises salt from about 140 mg/dL to about 180 mg/dL.

9. The method of claim 6, wherein the analyte concentration varies from an actual concentration of the analyte in the blood by +/−10% or less, and wherein the blood has a temperature from about 6° C. to about 44° C.

10. The method of claim 6, wherein the analyte concentration varies from an actual concentration of the analyte in the blood by +/−10% or less, wherein the blood comprises (a) hematocrit from about 20% to about 70% , and (b) salt from about 140 mg/dL to about 180 mg/dL, and wherein the blood has a temperature from about 6° C. to about 44° C.

11. The method of claim 1, wherein magnitude and shape of the excitation current response information and the response current response information are defined by points in an x-y space, wherein x=ln(time) and y=ln(current).

12. The method of claim 1, wherein the electrical test sequence further comprises an alternating current (AC) block, and the glucose concentration is further determined based on an effective phase and an effective admittance determined in an AC block current response.

13. The method of claim 12, wherein the glucose concentration is determined in accordance with the following equation:

$$\text{Predglu} = a0 + (b0 + \exp(b1 + b2 * I_{\text{eff}} + P_{\text{eff}} + Y_{\text{eff}})) * (I_{\text{eff}}),$$

wherein a0, b0, b1, and b2 are optimized constants, $I_{\text{eff}}$ is the effective current, $P_{\text{eff}}$ is the effective phase of the AC block current response, and $Y_{\text{eff}}$ is the effective admittance of the AC block current response.

14. The method of claim 13, wherein $P_{\text{eff}}$ is determined in accordance with the equation:

$$P_{\text{eff}} = bp2 * (p11 * \cos(\alpha) + p12 * \sin(\alpha)) + bp3 * (-p11 * \sin(\alpha) + p12 * \cos(\alpha)),$$

wherein $\alpha = \arctan(1)$, p11 is a 20 kHz AC phase, p12 is a 10 kHz AC phase, and bp2 and bp3 are optimized weighting coefficients.

15. The method of claim 13, wherein $Y_{\text{eff}}$ is determined in accordance with the equation:

$$Y_{\text{eff}} = by2 * (y11 * \cos(\alpha) + y12 * \sin(\alpha)) + by3 * (-y11 * \sin(\alpha) + y12 * \cos(\alpha)),$$

wherein $\alpha = \arctan(1)$, y11 is a 20 kHz AC admittance, y12 is a 10 kHz AC admittance, and by2 and by3 are optimized weighting coefficients.

16. The method of claim 12, wherein the glucose concentration is determined in accordance with the following equation:

$$\text{Predglu} = a0 + a1 * I_{\text{eff}} + \exp(b0 + P_{\text{eff}} + Y_{\text{eff}}) * I_{\text{eff}},$$

wherein a0, a1, and b0 are optimized constants, $I_{\text{eff}}$ is the effective current, $P_{\text{eff}}$ is the effective phase of the AC block current response, and $Y_{\text{eff}}$ is the effective admittance of the AC block current response.

17. The method of claim 1 wherein the glucose concentration is determined in accordance with the following equation:

$$\text{Predglu} = a0 + (b0 + \exp(b1 + b2 * I_{\text{eff}})) * (I_{\text{eff}}),$$

wherein a0, b0, b1, and b2 are optimized constants and $I_{\text{eff}}$ is the effective current.

18. The method of claim 1, wherein the glucose concentration is determined in accordance with the following equation:

$$\text{Predglu} = a0 + a1 * I_{\text{eff}} + \exp(b0) * I_{\text{eff}},$$

wherein a0, a1, and b0 are optimized constants and $I_{\text{eff}}$ is the effective current.

* * * * *